United States Patent [19]
Nickell

[11] 3,994,712
[45] Nov. 30, 1976

[54] RIPENING OF SUGARCANE BY USE OF CERTAIN MONOSUBSTITUTED BENZOIC ACIDS

[75] Inventor: Louis G. Nickell, Ellicott City, Md.

[73] Assignee: Hawaiian Sugar Planters' Association, Honolulu, Hawaii

[22] Filed: June 6, 1975

[21] Appl. No.: 584,341

[52] U.S. Cl. .................................. 71/105; 71/76; 71/115
[51] Int. Cl.² ........................................ A01N 9/24
[58] Field of Search .................... 71/105, 115, 76

[56] References Cited
UNITED STATES PATENTS
3,767,377  10/1973  Poulos .................................. 71/107

OTHER PUBLICATIONS
Abraham et al. Chem. Abst. vol. 70 (1969) 3477s.
Lobov et al. Chem. Abst. vol. 67 (1967) 63180n.
Pilet et al. Chem. Abst. vol. 64 (1966) 14877b.
Lee et al. Chem. Abst. vol. 63 (1965) 4877e.

*Primary Examiner*—Lewis Gotts
*Assistant Examiner*—Catherine L. Mills
*Attorney, Agent, or Firm*—Burns, Doane, Swecker & Mathis

[57] ABSTRACT

Sucrose yield of sugarcane is increased by treating sugarcane a few weeks prior to harvest with a monosubstituted benzoic acid sugarcane ripening agent selected from the group consisting of 2-chlorobenzoic acid, 3-hydroxybenzoic acid, 3-cyanobenzoic acid and 4-methoxybenzoic acid and mixtures thereof.

9 Claims, No Drawings

RIPENING OF SUGARCANE BY USE OF CERTAIN MONOSUBSTITUTED BENZOIC ACIDS

BACKGROUND OF THE INVENTION

Considerable progress has been made in the last several years in increasing the yield of sugarcane by improving the varieties being planted, enriching the soil with fertilizers and irrigating the soil in climates which do not naturally provide sufficient moisture for optimum plant growth. More recent efforts in improving sugar production have increasingly turned toward the use of chemicals in modifying the controlling of the physiological processes of sugarcane, particularly in ripening prior to harvest. See U.S. Pat. Nos. 3,244,865; 3,245,775; 3,291,592; 3,482,959; 3,482,961; 3,493,361; 3,505,056; 3,660,072 and 3,671,219.

With some compounds previously suggested for this purpose, there has been some concern about their resistance to breakdown in the plant and their persistence in the soil when the intended use of the sugar is nutritive as opposed to industrial (e.g., in fermentation processes). Consequently, extensive efforts continue to be made in searching for effective chemical agents that can be used to modify the ripening of sugarcane so as to increase the sucrose yield therefrom.

Certain polysubstituted benzoic acid compounds, for example, the dimethylamine salt of 2,3,6-trichlorobenzoic acid and alkyl esters of 2-methoxy-3,6-dichlorobenzoic acid, have been found to be effective sugarcane ripening agents. The dimethylamine salt of 2,3,6-trichlorobenzoic acid compound, however, not only has high hormonal and herbicidal activity on many plants, it also tends to possess an unacceptable stability which may result in a residue in the treated crop at a level greater than that which may be established as the maximum allowable. See, for example, "Sugarcane Ripening with Chemicals", Nickett et al., 1967 Reports, Hawaiian Sugar Technologists, pp. 104 to 109 at page 105. The alkyl esters of 2-methoxy-3,6 dichlorobenzoic acid compounds possess high volatility, relatively high ultraviolet instability, and poor reproducibility of results in field use.

Generally speaking, chemicals selected for evaluation have been of types which have been previously found active in work with other plants as plant hormones, herbicides or inhibitors of growth of terminal buds, or active in killing the spindle or cane upon topical micro-application, etc. However, among the compounds heretofore found to be useful for such other special purposes, surprisingly few have been found effective in controlling the ripening of sugarcane in the desirable manner. No predictable relationship has been recognized to date between (a) the chemical structure of such compounds, (b) their phytotoxic effects, or (c) their physiological effects on the morphogenetic development of the plant, and their activity in having positive effects on ripening. In other words, the effectiveness of a compound in controlling the ripening of sugarcane and thereby increasing sugar yield remains essentially unpredictable, and the search for suitable agents continues to be fundamentally empirical.

OBJECTS OF THE INVENTION

It is an object of this invention to provide new agents for controlling the ripening of sugarcane. A more specific object is to increase the sucrose yield of sugarcane by chemically treating it during its final ripening stages prior to harvest without introducing substantial toxicological hazards, and preferably without causing any visible damage to the cane plant such as drying of the spindle or other leaf.

Still more specifically, it is an object to increase the sucrose yield of sugarcane by treating it prior to harvest with a chemical agent which is sufficiently stable to provide the desired effect over a period of several weeks and thus give adequate operational flexibility, but which has a relatively low degree of persistence and is susceptible to autodecomposition or decomposition by soil bacterial. Compounds which increase the sucrose content of sugarcane only temporarily over a period of two or three weeks after application and then result in a substantial decrease are generally not desirable for the intended purpose.

SUMMARY OF THE INVENTION

It has now been discovered that excellent results in increasing the sucrose yield of sugarcane can be obtained by applying a monosubstituted benzoic acid sugarcane ripening agent taken from the group consisting of 2-chlorobenzoic acid, 3-hydroxybenzoic acid, 3-cyanobenzoic acid and 4-methoxybenzoic acid and mixtures thereof to the cane at a time at least about two weeks and up to about ten weeks before harvest. 3-hydroxybenzoic acid appears to be the most active of these compounds as thus is preferred.

DESCRIPTION OF SPECIFIC EMBODIMENTS

The 2-chlorobenzoic acid, 3-hydroxybenzoic acid 4-methoxybenzoic acid, and 3-cyanobenzoic acid compounds utilized in the process of the present invention are solids (melting points of 137°, 200°, 184° and 223° C., respectively). These sugarcane ripening agents are generally applied to the sugarcane in an aqueous medium. 3-hydroxybenzoic acid and 3-cyanobenzoic acid are water-soluble but 2-chlorobenzoic acid and 4-methoxybenzoic acid are water-insoluble. The latter may be utilized in suspension in water utilizing one or a combination of known surface active agents commonly and variously used in the prior art as wetting agents, detergents or emulsifying agents. However, dry dusting compositions containing any of the sugarcane ripening agents and a solid diluent such as clay are also useful.

Good results are obtained when the sugarcane crop is treated at a rate in the range of from about 1 to about 40 pounds of the active ingredient per acre of sugarcane, though higher rates of up to about 80 pounds or more per acre as well as rates lower than 1 pound per acre can be used. The optimum amount will vary somewhat depending on the specific treating composition applied.

In accordance with this invention, the sugarcane crop is treated with the sugarcane ripening agent at any time from 2 to 10 weeks before harvest, the preferred time for treatment being between about 3 and 8 weeks prior to harvest.

The sugarcane ripening agent is conveniently applied in the field in the form of an aqueous solution or suspension, e.g., a liquid composition which may be sprayed from a boom-spray or a solid dust composition where the active compound is diluted with an inert solid such as clay and which can be applied as a dust from an airplane.

With the type of boom-spray apparatus used in this work, it has been found convenient to apply the active ingredient to the sugarcane field in the form of an aqueous solution, suspension or emulsion having a concentration of active agent such that the application at a rate of from 5 to 20 gallons of liquid composition per acre will provide the required dosage of active chemical. However, the use of lower or higher gallonages may be preferred when a different dispensing mechanism is used.

Water is the preferred liquid carrier for the active sugarcane ripening agents in practicing the present invention. Instead of using water as the carrier, non-phytotoxic mineral oils either as such or in the form of water-in-oil or oil-in-water emulsions may be used similarly in accordance with practices which are common in the art of treating vegetation with beneficial growth control agents. Other active ingredients are not required and are preferably omitted with the 2-chlorobenzoic acid, 3-hydroxybenzoic acid, 3-cyanobenzoic acid or 4-hydroxybenzoic acid being present as essentially the sole active ingredient in the solution or suspension. Mixtures of these compounds may also be utilized.

While 2-chlorobenzoic acid, 3-hydroxybenzoic acid, 3-cyanobenzoic acid and 4-hydroxybenzoic acid exhibit substantial sugarcane ripening activity it has been found that isomers of these compounds and most other monosubstituted benzoic acids are unsuitable for use as sugarcane ripening agents. That is, while 3-hydroxybenzoic acid has been found to be a very effective sugarcane ripening agent, 2-hydroxybenzoic acid does not show any activity as a sugarcane ripening agent. Other monosubstituted benzoic acids such as, for example, 2-phenoxybenzoic acid, 4-acetamidobenzoic acid, 2-acetylbenzoic acid, 2-fluorobenzoic acid, 2-benzoylbenzoic acid and 2-f-chlorobenzoyl have been found to give negative results as sugarcane ripening agents while a number of other monosubstituted benzoic acid compounds such as, for example, 2-ethoxybenzoic acid, 4-methylaminobenzoic acid, 2-f-hydroxyphenylazobenzoic acid, 2-n-butoxybenzoic acid and others, either show no activity or insufficient activity as sugarcane ripening agents.

The invention is additionally illustrated in connection with the following Examples which are to be considered as illustrative of the present invention. It should be understood, however, that the invention is not limited to the specific details of the Examples.

EXAMPLE I 3-hydroxybenzoic acid, 2-chlorobenzoic acid and 4-methoxybenzoic acid are deposited or dropped by means of a syringe with a fine needle on the spindle area at the top of the last visible dewlap of each 20 stalks of sugarcane aged 18.25 months. (A dewlap is the junction between the blade of the leaf and the leaf sheath which clasps the stalk.) The stalks are contacted with about 38 mg./stalk deposits of the 3-hydroxybenzoic, 2-chlorobenzoic acid and 4-methoxybenzoic acid sugarcane ripening agents which corresponds to an application rate of about 4 pounds of the agent per acre of sugarcane. Ten of the stalks are harvested 4 weeks after such treatment and 10 more are harvested 5 weeks after such treatment. A similar treatment is made of each of 20 of the same sugarcane stalks with a 0.6 ml. dispersion of a solution containing Trysben, a known sugarcane ripening agent, which is the dimethylamine salt of 2,3,6-trichlorobenzoic acid. The Trysben is applied in the form of a 50 percent aqueous solution containing about 0.25 percent (w/w) nonylphenol which is ethoxylated to contain about 10.5 moles of ethylene oxide per mole of nonylphenol.

The top 15 joints of the treated cane as well as those of similar untreated cane are removed, combined and analyzed in terms of juice purity and pol percent cane, following the so-called "press method" developed by T. Tanimoto, Hawaiian Planters Record, 57, 133 (1964). "Pol percent cane" is a polarimetric determination and equals the percentage of sucrose if the latter is the only substance in the solution which will rotate the plane of polarized light. In any event, determination of the pol percent cane is a standard and effective method for determining the sucrose content of sugarcane.

The results are given below:

|  | Time From Treatment to Harvest | | | |
|---|---|---|---|---|
|  | Four Weeks | | Five Weeks | |
|  | Juice Purity | Pol Percent Cane | Juice Purity | Pol Percent Cane |
| Control (untreated) | 65.00 | 7.03 | 72.50 | 8.20 |
| Standard (Trysben) | 58.53 | 5.59 | 76.02 | 9.64 |
| 3-hydroxybenzoic acid | 82.89 | 12.39 | 83.23 | 12.19 |
| 2-chlorobenzoic acid | 71.47 | 8.21 | 81.26 | 11.55 |
| 4-methoxybenzoic acid | 77.75 | 10.39 | 75.84 | 9.97 |

As is apparent, the application of the sugarcane ripening agents of the present invention result in a very substantial improvement in both juice purity and pol percent cane. Treatment of the cane with mixtures of these compounds (total active material applied at a rate of 4 pounds per acre) yields similar improved results.

EXAMPLE II

The procedure of Example I is repeated on stalks 22.25 months of age in a different field with both 19 mg./stalk (about 2 pounds/acre) and 38 mg./stalk deposits (about 4 pounds/acre) of 3-hydroxybenzoic acid and 38 mg./stalk deposits (about 4 pounds/acre) of 2-chlorobenzoic acid except that all of the stalks are harvested five weeks after treatment. The following results are obtained.

|  | From Treatment to Harvest | |
|---|---|---|
|  | Five Weeks | |
|  | Juice Purity | Pol Percent Cane |
| Control (untreated) | 54.64 | 4.86 |
| Standard (Trysben) | 76.94 | 10.46 |
| 3-hydroxybenzoic acid (38 mg/stalk) | 73.95 | 9.16 |
| 3-hydroxybenzoic acid (19 mg/stalk) | 66.37 | 7.17 |
| 2-chlorobenzoic acid (38 mg/stalk) | 65.38 | 6.37 |

A very apparent improvement in sucrose yield and juice purity results.

EXAMPLE III

Example II is repeated on stalks 20.75 months of age with 38 mg/stalk deposits (about 4 pounds/acre) of 3-hydroxybenzoic acid with the following results.

|  | From Treatment to Harvest Five Weeks | |
|---|---|---|
|  | Juice Purity | Pol Percent Cane |
| Control (untreated) | 70.00 | 7.10 |
| Standard (Trysben) | 76.30 | 8.80 |
| 3-hydroxybenzoic acid | 74.20 | 8.70 |

Again, the improvement in sucrose yield and juice purity is apparent.

EXAMPLE IV

The procedure of Example II is repeated utilizing 3-cyanobenzoic acid on stalks 15.75 months of age in amounts of 38 mg/stalk deposits (about 4 pounds/acre) with the following results.

|  | From Treatment to Harvest Five Weeks | |
|---|---|---|
|  | Juice Purity | Pol Percent Cane |
| Control (untreated) | 62.62 | 7.06 |
| Standard (Trysben) | 73.95 | 9.71 |
| 3-cyanobenzoic acid | 69.15 | 8.45 |

EXAMPLE V

Example IV is repeated on stalks 21.5 months of age in amounts of 38 mg/stalk (about 4 pounds/acre) with the following results:

|  | From Treatment to Harvest Five Weeks | |
|---|---|---|
|  | Juice Purity | Pol Percent Cane |
| Control (untreated) | 73.50 | 8.86 |
| Standard (Trysben) | 83.17 | 10.77 |
| 3-cyanobenzoic acid | 79.78 | 10.08 |

Again, the results show that an increase in yield and purity of sugar are obtained.

COMPARATIVE EXAMPLES

Field growing sugarcane is contacted in the manner of Example I with aqueous solutions of monosubstituted benzoic acids. The results obtained in qualitative terms are shown below. In these results, a minus sign "−" means that the treated cane yielded less sugar (that is, a lower pol percent cane) than the control sample, a zero "0" means that the treated cane showed essentially the same sugar yield, a single plus sign "+" means that the treated cane showed a minor increase in sugar yield while a double plus sign "++" means that the treated cane showed an increase that is recognizable in sugar yield but insufficient to be considered useful for practical application. The monosubstituted benzoic acid compounds tested are identified in the following table by substituent and position on the benzene ring.

TABLE 6

| Substituent | Activity, Position | | |
|---|---|---|---|
|  | 2 or 6 | 3 or 5 | 4 |
| hydroxy | 0 |  | + |
| nitro |  | ++ |  |
| methoxy | ++ |  |  |
| amino |  | + | + |
| methylamino |  |  | 0 |
| iodo | 0 | ++ |  |
| bromo | + |  | 0 |
| fluoro | − |  |  |
| chloro |  |  | ++ |
| acetoxy | ++ |  |  |
| p-chlorobenzoyl | − |  |  |
| sulfamyl |  |  | 0 |
| benzoyl | − |  | 0 |
| acetyl | − |  |  |
| n-butoxy |  |  | 0 |
| chloromercuri |  |  | + |
| p-fluorobenzoyl | + |  |  |
| fluorosulfonyl |  |  | ++ |
| p-chlorophenyl sulfonyl |  |  | 0 |
| phthalimido | ++ |  |  |
| acetamido |  |  | − |
| chloroperoxy |  | + |  |
| ethoxy | 0 |  |  |
| p-hydroxyphenylazo | 0 |  |  |
| b-butyl |  |  | + |
| anthraniloyl | 0 |  |  |
| phenoxy | − |  |  |

The nature, scope, utility and effectiveness of the present invention have been described and specifically exemplified in the foregoing specification. However, it should be understood that these examples are not intended to be limiting and that the true scope of the invention to be protected is particularly pointed out in the appended claims.

What is claimed is:

1. A process for increasing the sugar yield of grown sugarcane which comprises applying a monosubstituted benzoic acid sugarcane ripening agent taken from the group consisting of 2-chlorobenzoic acid, 3-hydroxybenzoic acid, 3-cyanobenzoic acid, 4-methoxybenzoic acid and mixtures thereof to the cane at a time at least about two weeks and up to about ten weeks prior to harvest.

2. The process of claim 1 wherein the monosubstituted benzoic acid sugarcane ripening agent is 4-methoxybenzoic acid.

3. The process of claim 1 wherein the monosubstituted benzoic acid sugarcane ripening agent is 2-chlorobenzoic acid.

4. The process of claim 1 wherein the monosubstituted benzoic acid sugarcane ripening agent is 3-hydroxybenzoic acid.

5. The process of claim 1 wherein the monosubstituted benzoic acid sugarcane ripening agent is 3-cyanobenzoic acid.

6. A process according to claim 1 wherein said sugarcane ripening agent is applied to the cane at a rate corresponding to from about 1 to about 80 pounds per acre.

7. A process according to claim 1 wherein the compound is applied to the cane at a time of between about 3 and 8 weeks before harvest.

8. A process according to claim 6 wherein said sugarcane ripening agent is applied to the cane at a rate corresponding to from about 1 to about 40 pounds per acre.

9. A process according to claim 1 wherein the sugarcane ripening agent is applied to the cane at a rate of from 1 to about 40 pounds per acre and at a time of between about 3 and about 8 weeks before harvest.

* * * * *